(12) United States Patent
Shennib et al.

(10) Patent No.: US 6,940,989 B1
(45) Date of Patent: Sep. 6, 2005

(54) DIRECT TYMPANIC DRIVE VIA A FLOATING FILAMENT ASSEMBLY

(75) Inventors: Adnan Shennib, Fremont, CA (US); Robert Schindler, San Francisco, CA (US); Richard C. Urso, Redwood City, CA (US)

(73) Assignee: InSound Medical, Inc., Newark, CA (US)

( * ) Notice: Subject to any disclaimer, the term of this patent is extended or adjusted under 35 U.S.C. 154(b) by 0 days.

(21) Appl. No.: 09/475,923

(22) Filed: Dec. 30, 1999

(51) Int. Cl.[7] .............................................. H04R 25/00
(52) U.S. Cl. ........................ 381/326; 381/328; 600/25
(58) Field of Search ............................... 381/23.1, 312, 381/314, 324, 326, 328–329, 151; 181/128–130, 134–135; 600/25, 559; 623/10; 29/896.21

(56) References Cited

U.S. PATENT DOCUMENTS

| | | | |
|---|---|---|---|
| 2,164,121 A | * 6/1939 | Pescador | 381/328 |
| 3,594,514 A | * 7/1971 | Wingrove | 381/328 |
| 3,764,748 A | 10/1973 | Branch et al. | |
| 3,870,832 A | 3/1975 | Fredrickson | |
| 3,882,285 A | 5/1975 | Nunley et al. | |
| 4,505,329 A | 3/1985 | Hough | |
| 4,628,907 A | 12/1986 | Epley | |
| 4,756,312 A | 7/1988 | Epley | |
| 4,776,322 A | 10/1988 | Hough et al. | |
| 4,817,607 A | 4/1989 | Tatge | |
| 4,840,178 A | 6/1989 | Heide et al. | |
| 4,957,478 A | 9/1990 | Maniglia | |
| 5,015,225 A | 4/1991 | Hough et al. | |
| 5,015,224 A | 5/1991 | Maniglia | |
| 5,163,957 A | 11/1992 | Sadé et al. | |
| 5,220,918 A | * 6/1993 | Heide et al. | 128/420.6 |
| 5,259,032 A | * 11/1993 | Perkins et al. | 381/328 |
| 5,282,858 A | 2/1994 | Bisch et al. | |
| 5,338,287 A | * 8/1994 | Miller et al. | 600/25 |
| 5,425,104 A | 6/1995 | Shennib | |
| 5,456,654 A | 10/1995 | Ball | |
| 5,531,787 A | 7/1996 | Lesinski et al. | |

(Continued)

OTHER PUBLICATIONS

US 5,730,699, 3/1998, Adams et al. (withdrawn)
Chasin, Marshall, *CIC Handbook*, Singular Publishing Group, Inc., (1997) pp. 12–14, 17–18, 27–28, 44, 56–58, 65–66.

(Continued)

*Primary Examiner*—Curtis Kuntz
*Assistant Examiner*—P. Dabney
(74) *Attorney, Agent, or Firm*—Townsend and Townsend and Crew LLP.

(57) ABSTRACT

A canal hearing device has a subminiature filament assembly which vibrates and directly drives the tympanic membrane (eardrum) and imparts audible mechanical vibrations thereto. The filament assembly is partially supported by the tympanic membrane via capillary adhesion thereto and is dynamically coupled to a stationary vibration force element position at a distance from the tympanic membrane within the ear canal. The elongated filament assembly is freely movable within an operable range and is essentially floating with respect to the vibration force element. In a preferred embodiment, the vibrational filament assembly comprises a magnetic section which is insertable into the air-core of an electromagnetic coil. The filament assembly is coupled to the tympanic membrane via an articulated tympanic contact coupler.

92 Claims, 8 Drawing Sheets

U.S. PATENT DOCUMENTS

| | | |
|---|---|---|
| 5,554,096 A | 9/1996 | Ball |
| 5,624,376 A | 4/1997 | Ball et al. |
| 5,654,530 A | 8/1997 | Sauer et al. |
| 5,682,020 A | 10/1997 | Oliveira |
| 5,701,348 A | 12/1997 | Shennib et al. |
| 5,797,834 A * | 8/1998 | Goode ......................... 600/25 |
| 5,833,626 A * | 11/1998 | Leysieffer ................... 600/559 |
| 6,137,889 A * | 10/2000 | Shennib et al. ............. 381/328 |
| 6,408,081 B1 | 6/2002 | Boesen |
| 6,620,110 B2 | 9/2003 | Schmid |
| 6,643,378 B2 | 11/2003 | Schumaier |
| 6,648,813 B2 | 11/2003 | Zilberman et al. |
| 6,658,126 B1 | 12/2003 | Stern |

OTHER PUBLICATIONS

Oliveira, Robert J., Navarro, Richard, "The Wax Problem: Two New Approaches," *The Hearing Journal* (Aug. 1993) vol. 46, No. 8, pp. 41–46.

* cited by examiner

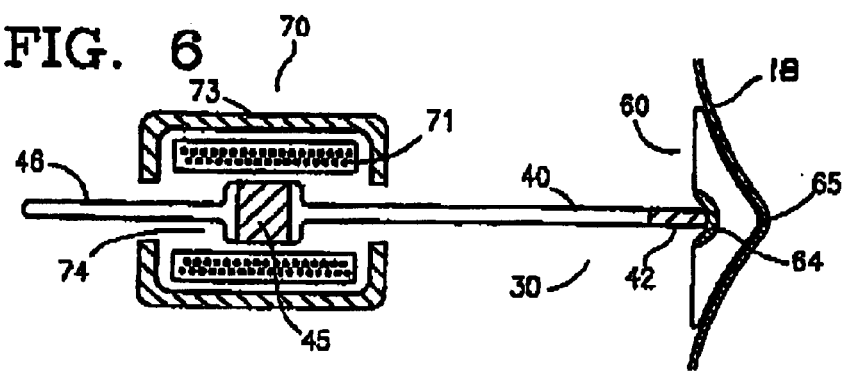
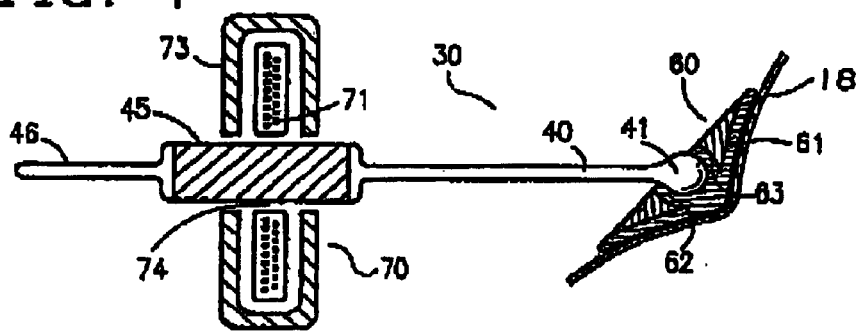
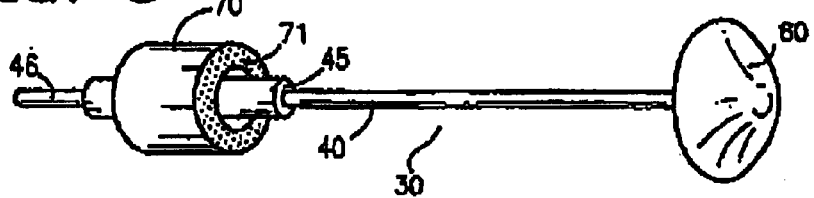
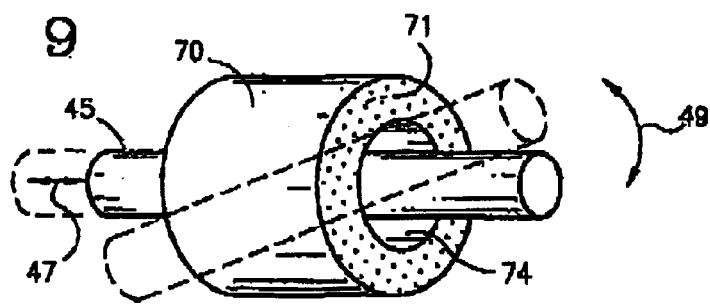

DIRECT TYMPANIC DRIVE VIA A FLOATING FILAMENT ASSEMBLY

CROSS-REFERENCE TO RELATED APPLICATION

This application is related to commonly assigned patent application Ser. No. 09/085,486, filed May 27, 1998, titled "Direct Tympanic Membrane Excitation Via Vibrational Conductive Assembly", referred to herein as "the '486 application".

BACKGROUND OF THE INVENTION

The present invention relates generally to transducers for converting audio signals to audible mechanical vibrations, and more particularly to hearing devices with improved energy efficiency, sound fidelity, and inconspicuous wear.

The external acoustic means (ear canal) is generally narrow and contoured as shown in the coronal view in FIG. 1. The ear canal 10 is approximately 27 mm in length from the canal aperture 17 to the center of the tympanic membrane 19 (eardrum). The lateral part (away from the tympanic membrane) of the ear canal, a cartilaginous region 11, is relatively soft due to the underlying cartilaginous tissue. The cartilaginous region 11 of the ear canal 10 deforms and moves in response to the mandibular (jaw) motions, which occur during taking, yawning, eating, etc. The medial (towards the tympanic membrane) part, a bony region 13 proximal to the tympanic membrane, is rigid due to the underlying bony tissue. The skin 14 in the bony region 13 is thin (relative to the skin 16 in the cartilaginous region) and is more sensitive to touch or pressure. There is a characteristic bend 15 that roughly occurs at the bony-cartilaginous junction 19 (referred to herein as the bony junction), which separates the cartilaginous 11 and the bony 13 regions. The magnitude of this bend varies among individuals.

Hair 5 and debris 4 in the ear canal are primarily present in the cartilaginous region 1. Physiologic debris includes cerumen (earwax), sweat, exfoliated skin and hair, and oils produced by the various glands underneath the skin in the cartilaginous region. Non-physiologic debris consists primarily of environment particles that enter the ear canal. Canal debris is naturally extruded to the outside of the ear by the process of lateral epithelial cell migration that begins on the eardrum and extends the length of the ear canal (see. e.g., Ballachanda, *The Human ear Canal,* Singular Publishing, 1995, pp. 78, 195). There is no cerumen production or hair in the bony part of the ear canal.

The ear canal 10 terminates medially with the tympanic membrane 18 which has a characteristic conical depression at its center—known as the umbo 20. Laterally and external to the ear canal is the concha cavity 2 and the auricle 3, both also cartilaginous. The junction between the concha cavity 2 and the cartilaginous part 11 of the ear canal at the aperture 17 is also defined by a characteristic bend 12 known as the first bend of the ear canal.

The tympanic membrane is medially connected to the handle of the malleus ossicle 21 (FIG. 2) which is connected to the incus 22, stapes 23 and ligaments and muscles (not shown) within the middle ear cavity 25. The tympanic membrane 18 and associated middle ear ossicles 21, 22 and 23 are extremely sensitive to pressure waves which are imperceptible by even the most delicate receptors of skin.

Hearing loss affects a substantial percentage of the population, and is of several types. Hearing loss occurs naturally with aging, beginning with the higher frequencies (4000 Hz and above) and increasingly spreads to lower frequencies. Conductive losses attributable to obstruction of the transmission of mechanical vibrations in the middle ear or the tympanic membrane also effect the hearing. It is customary, of course, to fit individuals who suffer from hearing loss with hearing aid devices if they cannot be treated with medication or surgery.

In general, conventional hearing aids rely primarily on air-conduction transducers to produce amplified acoustic pressure waves which are transmitted to the tympanic membrane through the air between the transducer and the tympanic membrane. These transducers, also referred to as receivers or speakers, are used in various audio devices including telephones, and other communication devices. Recent advances in miniaturization have led to new types of hearing aids that fit deeply in the ear canal, with receivers close to the tympanic membrane. Such devices are largely inconspicuous, and thereby tend to alleviate the social stigma and vanity concerns associated with wearing a visible hearing aid, which are considered a significant obstacle to hearing aid use among the hearing impaired population. Nevertheless, a number of fundamental limitations remain in hearing devices that utilize air-conduction based technology, including problems of (1) frequency, daily device handling, (2) acoustic feedback, (3) ear canal occlusion, and (4) low sound fidelity.

The problem of frequent conventional device handling relates to frequent insertion and removal from the ear canal. Conventional hearing aids are typically removed daily to relieve the ear canal from contact pressure. The requirement of frequent handling, particularly with miniature hearing devices, poses a serious challenge to potential users who suffer physical impairment beyond hearing loss because of age or disorders, such as arthritis, tremors, or other neurologic problems. Frequent hearing air removal is also required to replace the battery. For miniature canal devices (the term "canal devices" refers to miniature hearing devices that are primarily fitted in the ear canal, and includes the industry-recognized "In-The-Canal" (ITC) devices and "Completely-In-the-Canal" (CIC) devices), typical battery lifetimes range from few days to two weeks. The need for frequent battery replacement is attributable in large part to the magnitude of energy consumption by conventional air-conduction receivers (speakers).

The problem of acoustic feedback occurs when a portion of the sound output, typically from a receiver (speaker), leaks to the input of the hearing system such as a microphone of a hearing aid. Such leakage often causes a sustained oscillation which is manifested by "whistling" or "squealing". Acoustic feedback is not only annoying to hearing aid users but also interferes with their speech communication. Feedback is a common occurrence in conventional hearing aids since the output of the device (acoustic) is in the same form of energy as the input of the device (also acoustic). Feedback is typically alleviated by occluding (sealing) the ear canal tightly with the hearing device. Whichever acoustic sealing method is used, ear canal occlusion causes an array of occlusion-related side effects.

Occlusion related problems include discomfort, irritation and even pain; moisture building-up in the occluded ear canal; cerumen impaction; and acoustic occlusion effect, Discomfort, irritation and pain may occur from canal abrasion caused by frequent insertion and removal of a tightly fitted hearing device. Moisture build-up in the occluded ear canal can cause infection in the ear canal as well as damage to the hearing device within. To reduce possible damaging effects of anal moisture, it is recommended that hearing devices be removed daily.

Another important problem is cerumen impaction (i.e., blockage of the ear canal by earwax) which occurs when ear wax is pushed deeper in the ear canal by the frequent insertion of a hearing device. Cerumen can also build up on the receiver of the hearing device, thereby causing frequent malfunction.

The occlusion effect is a common acoustic problem caused by the occluding hearing device, manifested by the perception of a person's own-voice ("self-voice") being loud and unnatural compared to that with the open ear canal. This phenomenon is sometimes referred to as the "barrel effect" since it resembles the experience of talking into a barrel.

Low or inadequate sound fidelity is often experienced with air-conduction receivers (speakers), particularly in hearing aid applications where the frequency response is limited to about 5000 Hz.

Considering the state of the art in alternative hearing device technology, hearing devices employing transducers that are not based on air-conduction are well known in the art. The rationale is that when no acoustic output is present in such devices, oscillatory feedback is usually reduced and in most cases eliminated. Distortion and frequency response characteristics are also potentially improved.

For example, vibratory middle ear implants attempt to circumvent some of the above-cited limitations by vibrating directly any of the ossicular (middle ear bones) or cochlear structures. Vibratory transducers and hearing devices for middle ear implant are disclosed in numerous patents, e.g., U.S. Pat. Nos. (U.S. Pat. Nos.) 3,594,514 to Wingrove, 3,870,832 to Fredrickson, 3,882,285 to Nunley et al., 5,015,224 to Maniglia, and 5,554,096 and 5,456,654 to Ball. The transducer technology employed includes piezoelectric and electromagnetic elements, which provide electrical output via an electrical wire connection to the transducer. Disadvantages of middle ear implants include the cost and risk involved in the surgical procedure, and the additional surgery that may be required to repair device malfunctions or to replace an implanted battery.

Several other hearing systems that are less invasive have been proposed and are known in the art. Magnetic transducers which are surgically implanted or surgically attached to the tympanic membrane are disclosed in a number of patents, e.g., U.S. Pat. Nos. 4,840,178 and 5,220,918 to Heide et al., 4,817,607 to Tatge et al., 4,606,329, 4,776,322 and 5,015,225 to Hough et al., 4,957,478 to Maniglia, 5,163,957 to Sade et al., and 5,338,287 to Miller et al. These transducers typically employ high energy-product magnets which vibrate in response to a radiant electromagnetic signal, representative of acoustic signals. The electromagnetic signal is typically radiated by a coil positioned in the external ear canal (e.g., 44 of FIG. 1 in the Manigila '478 patent, and 28 of FIG. 1 in the Tatge '607 patent). Similarly, a primary disadvantage of this type of device is the cost and risk of surgery performed on the delicate vibratory structures of the ear.

Among others of the less invasive approaches to hearing systems are those proposed in U.S. Pat. Nos. 5,259,032 to Perkins et al., and 5,425,104 to Shennib. In each of these disclosures, a magnet transducer is attached non-surgically to the exterior side of the tympanic membrane, and transducer receives radiant electromagnetic signals from a device in the ear canal (FIG. 4 of the Perkins et al '032 patent), or from an externally positioned coil (FIGS. 1A and 1B of the Schennib '104 patent).

A major disadvantage with all of the above electromagnetic hearing systems is the inefficiency associated with transducing radiant electromagnetic energy into magnet vibrations, attributable to the relatively small portion of radiant electromagnetic energy produced by the coil that reaches the magnet. As is known in the art of electromagnetics, the efficiency of such coupling is inversely proportional to the distance between the driving coil and the magnet transducer. This and other limitations of such devices render the various modes of radiant electromagnetic transconduction impractical for most hearing aid applications.

A potentially more energy efficient transducer and hearing system is disclosed in U.S. Pat. No. 5,624,376 to Ball et al. In a non-invasive embodiment of the transducer disclosed in FIG. 19a of the Ball et al '376 patent, a floating mass transducer 100 is attached non-surgically to the exterior side of the tympanic membrane via an attachment membrane 502. The transducer 100 may be directly connected (not shown, but disclosed at col. 16, line 62) to a hearing device 506 via electrical wires 24. The "floating mass transducer" (FIG. 3), incorporates a magnet 42 (floating mass) and a coil 14 within a housing 10. The transducer 100 is free to vibrate within the housing 10 in response to the electrical signal via wires 24. The inertial forces of the vibrating magnet cause the housing to vibrate and subsequently vibrate the attached tympanic membrane and ossicles. According to the Ball et al '376 patent, vibrational forces are maximized by optimizing the mass of the magnet assembly relative to the combined mass of coil and housing, and the energy product of the permanent magnet. Since the transducer receives electrical energy directly from the hearing device via a wire, energy loss is reduced and the device is potentially more energy efficient than air-conduction or radiant electromagnetic hearing systems. However, a major disadvantage of the floating mass transducer is the weight of the transducer assembly being positioned directly on the tympanic membrane.

Another alternative to air-conduction hearing devices is disclosed in U.S. Pat. Nos. 4,628,907 and 4,756,312 to Epley. The Epley '907 patent describes a canal hearing device with an electromechanical transducer part directly contacting the tympanic membrane (FIG. 1), the contact element 38 being secured to the tympanic membrane by clip means for attachment to malleus bone (claim 1). The devices are not only invasive as disclosed, but also pose a considerable risk to the delicate structures of the tympanic membrane from inadvertent movement of the hearing device, which may occur, for example, simply by normal jaw motion.

Many of these prior art devices are either energy inefficient or occlusive to the ear canal which render them impractical for extended wear. As used in the present application, extended wear use means continuous placement and operation of a hearing device within the ear canal for at least two months.

Leysieffer in U.S. Pat. No. 5,833,626 describes a non-invasive hearing testing method involving vibrating the tympanic membrane via a rod placed within the ear canal. Leysieffer is primarily concerned with providing, temporarily, audiological test signal to the test ear while minimizing audibility by the contralateral ear which is not being examined. Clearly, Leysieffer's invention is not concerned with hearing devices and particularly devices for extended wear within the ear canal.

Shennib et al., in the aforementioned co-pending '486 application, describes a canal hearing device having a thin elongated vibrational assembly which directly contacts the tympanic membrane causing audible vibrations. The canal hearing device of that invention uses strain relief methods for minimizing static pressures on the tympanic membrane by the coupled vibrational assembly. However, device movements within the ear canal or changes in the atmospheric pressure affecting the position of the tympanic membrane, can cause considerable variations in the dynamic coupling and therefore the perceived sound. The effect of dynamic coupling due to changes in the static coupling is highly undesirable since it necessitates readjustment of the electroacoustic parameters (i.e., volume, frequency response, etc.) whenever changes in the static coupling occur.

A key goal of the present invention is to provide is to provide efficient sound conduction by vibrating the tympanic membrane directly and consistently regardless of the exact position of the canal hearing device with respect to tympanic membrane.

Another goal of the present invention is to position a vibration force transducer within the ear canal at a distance from the tympanic membrane thus minimize the mass loading effect on the tympanic membrane.

An other goal of the present invention is to offer an inconspicuous and non-occlusive energy efficient hearing device suitable for extended wear within the ear canal.

Extended wear as used in this specification and appended claims is defined as continuous placement and use of the hearing device within the ear canal without need for removal for at least about two months.

SUMMARY OF THE INVENTION

The present invention provides a canal hearing device having a miniature vibratory filament assembly which directly drives the tympanic membrane (eardrum) and imparts audible vibrations thereto. The filament assembly is partially supported by the tympanic membrane via weak adhesion thereto and is dynamically coupled to a stationary vibration force element positioned at a distance from the tympanic membrane within the ear canal. The elongated filament assembly is freely movable within an operable range and is essentially floating with respect to the vibration force element.

In a preferred embodiment of the invention, the vibrational filament assembly comprises a magnetic tip laterally, which is inserted into the air-core of a cylindrical force element comprised of an electromagnetic coil. The coil produces a magnetic field representative of audio signals, thus imparting vibrations on the magnetic filament assembly which subsequently conducts these vibrations to the tympanic membrane via the filament shaft. The electromagnetic coil is positioned concentrically over the magnetic filament assembly for an extremely energy efficient dynamic coupling. However, friction between the coil and the filament is minimal, thus allowing essentially friction-free axial movement for the filament assembly with respect to the stationary coil.

The filament assembly is coupled to the tympanic membrane via a tympanic contact coupler at its medial end. The tympanic contact coupler is conically-shaped for fitting into the umbo area, also conically-shaped. The tympanic contact coupler of the filament assembly is weakly attached to the umbo area via minimal adhesion forces between the surface of the tympanic contact coupler and the tympanic membrane. In a preferred embodiment, the surface adhesion between the tympanic pad and the tympanic membrane is enhanced by the application of an adhesion agent such as mineral oil or gel. The tympanic contact coupler is articulated with the shaft of the filament assembly via a subminiature ball joint system. The articulation of the tympanic coupler in conjunction with the friction-free axial movement of the filament assembly provides individual adjustment within the ear canal for properly contacting the tympanic membrane and imparting audible vibrations thereto. The dynamic coupling between the filament assembly and the force transducer essentially eliminates static forces on the tympanic membrane, thus offering safe and comfortable wear.

Since coupling to the tympanic membrane is vibrational rather than acoustic as with conventional hearing aids, acoustic feedback (whistling) is largely eliminated without restoring to a tight occlusive fit in the ear canal. The energy efficiency and non-occlusive design features of the invented hearing device allow for extended wear embodiments not possible with conventional acoustic hearing aids.

BRIEF DESCRIPTION OF THE DRAWINGS

The above and still further goals, objectives, features, aspects and attendant advantages of the present invention will be better understood from the following detailed description of the best mode presently contemplated for practicing the invention, with reference to certain preferred embodiments and methods, taken in conjunction with the accompanying Figures of drawing, in which:

FIG. 6 is a sectional side view of a vibrational filament assembly contacting the tympanic membrane having an alternate articulation method comprising a magnetic tip mating with a magnetic recess, and with the vibrating force coil shown cylindrically elongated;

FIG. 7 is a sectional side view of an alternate embodiment of the vibrating force coil having relatively short length (disk shaped);

FIG. 8 is a perspective vie of an alternate embodiment of the vibrating force coil having a magnetic tubular ring fitted over the shaft of the filament assembly;

FIG. 9 is a perspective partial view of a vibrational filament assembly moving in multi-dimensional degree of motion freedom with response to a vibration force element;

DETAILED DESCRIPTION OF THE PREFERRED EMBODIMENTS AND METHODS

Figure 1:
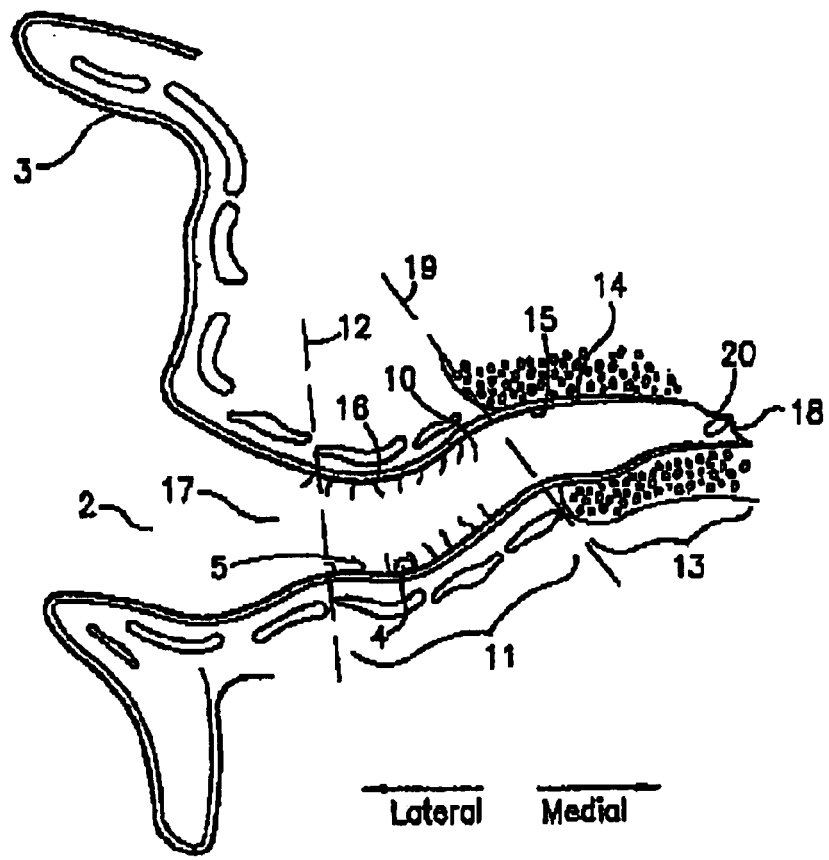
FIG. 1 in a coronal view of the external and middle ear showing the ear canal and the tympanic membrane, described above.
Figure 2:
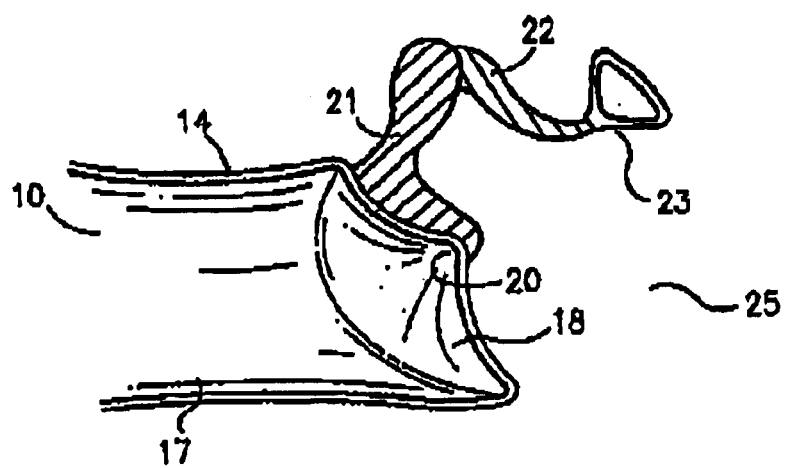
FIG. 2 is a sectional side view of the tympanic membrane and middle ear ossicles, showing the umbo area and malleus handle, described above.
Figure 3:
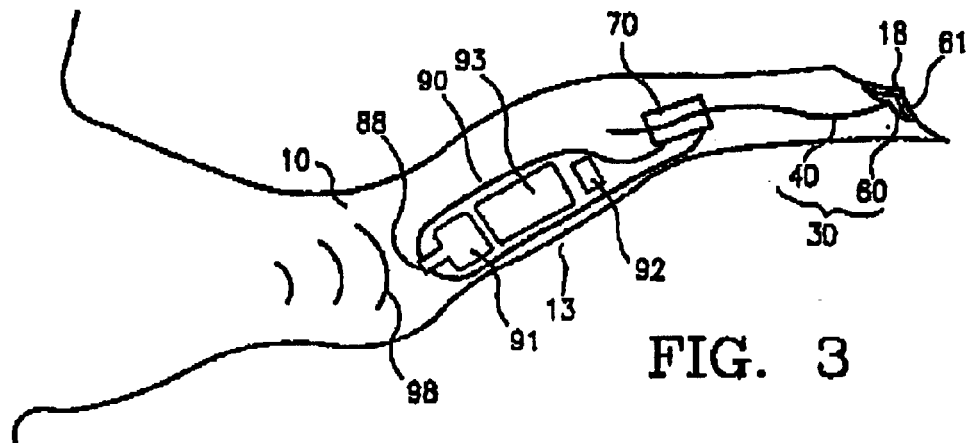
FIG. 3 is a sectional side view of a completely inconspicuous hearing device with an embodiment of the vibrational filament assembly of the present invention.

The present invention, illustrated in FIGS. 3–28, provides a vibrational filament assembly 30 to impart audible vibrations directly onto tympanic membrane 18 (e.g., FIG. 3). The filament assembly 30 consists of a thin elongate vibrational conductive member, referred to as filament shaft 40, and a tympanic coupling element, referred to as tympanic coupling pad 60, placed on the tympanic membrane 18 of a human subject (sometime referred to herein as the wearer of the hearing device, or simply, the wearer). The tympanic coupling pad 60 is weakly adhered to the tympanic membrane and is articulated with respect to the filament shaft 40 to allow for individual variations in the orientation of the tympanic membrane. The filament assembly 30 is dynamically coupled to a vibration force element 70 incorporated within a canal hearing device 90. The dynamic coupling allows the filament assembly 30 to move relatively freely axially with respect to the vibration force element 70 without adversely affecting the dynamic coupling therebetween. This freedom of movement allows for individual variations in the positioning of the hearing device 90 within the ear canal. The unique coupling arrangement between the vibration force element, the filament assembly 30 and the tympanic membrane 18 allows for consistent and energy efficient vibrational (dynamic) coupling while providing essentially no static pressure on the tympanic membrane, regardless of the exact position of the canal hearing device.

The hearing device in the preferred embodiments is completely positioned in the ear canal 10 substantially within the bony region 13 in proximity to the tympanic membrane 18 as shown in FIG. 3. The hearing device 90, configured as a hearing aid, contains a microphone 91 for receiving incoming acoustic signals 98 and transducing them to electrical signals, a processing amplifier 92 for processing and amplifying electrical signals from microphone 91, and a battery assembly 93. The amplified signal from processing amplifier 92 is delivered to a vibration force element 70 which imparts vibrations on the filament assembly 30 dynamically coupled to vibration force element 70. These vibrations are representative of the incoming acoustic signals 98. Although acoustic signals may be speed of persons with whom the wearer is engaged in conversation, other signals, more broadly referred to here as audio signals, may be received from a variety of wire and wireless sources including electromagnetic, radio frequency, ultrasonic and optical signals.

A hearing aid typically comprises other components such as adjustment controls for non-programmable hearing aids or a programming interface for programmable hearing aids. These components are well known in the art of hearing aid design and are thus not shown in the figures, for the sake of simplicity and clarity.

In a preferred embodiment of the invention, shown FIG. 3, hearing device 90 is completely and non-occlusively concealed within the ear canal for maximum cosmetic appeal. The hearing device is also designed for extended wear as made possible partially by the energy efficiency of the vibrational coupling mechanism of the present invention.

Figure 4:
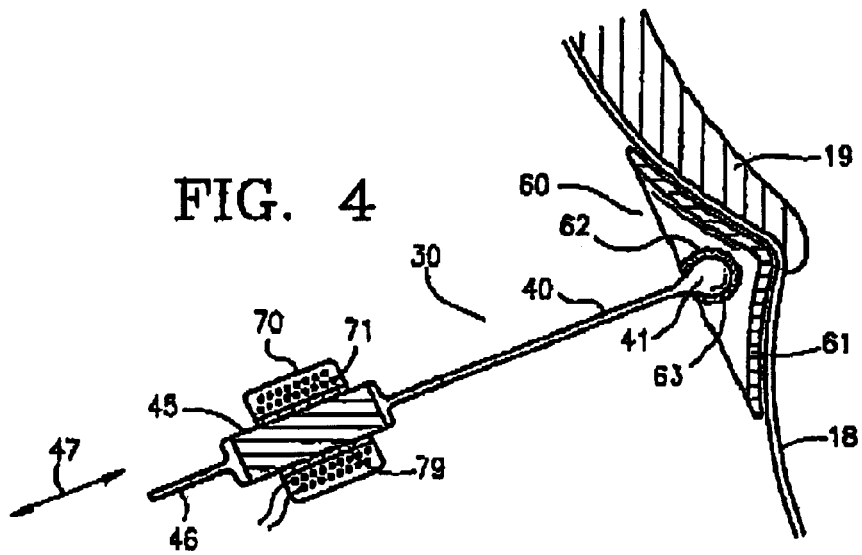
FIG. 4 is a detailed side view of the vibrational filament assembly in contact with the tympanic membrane, showing the tympanic coupling element articulating with the shaft, and magnetic vibratory element floating within the vibration force coil, in which the magnetic filament assembly is shown with one degree of motion freedom.
Figure 5:
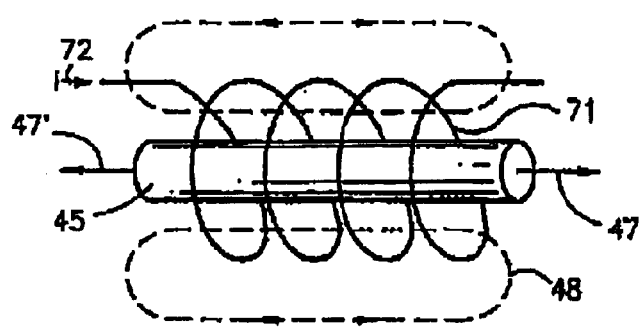
FIG. 5 is a partial schematic diagram of the magnetic filament assembly responsive to a magnetic field produced by an electromagnetic coil when a current flows through it, the magnetic field being representative of incoming acoustic (audio) signals.

The vibrational filament assembly 30, referred to herein as the filament assembly, and vibration force element 70 are shown in more detail in the exemplary embodiments of FIGS. 4–9. In the filament assembly of FIG. 4, filament shaft 40 is coupled to tympanic coupling pad 60 via an articulated ball-joint system with the medial tip of the shaft comprising a ball head 41 fitting into a ball socket 62 centrally positioned within the tympanic coupling pad 60. The filament assembly 30 comprises a vibratory element 45 which responds to vibration forces produced by vibration force element 70. In the preferred embodiments of the invention, shown in FIGS. 4–9, the vibratory element 45 is composed of a magnetic material (i.e., magnet, iron, etc.) which responds to dynamic magnetic field 48 (FIG. 5) produced by a coil 71. The magnetic field 48 is produced by coil 71 when an alternating current 72 (labeled i) representative of audio signals is introduced into the coil by the hearing device. The magnetic vibratory element 45 is free to move within the air-core of the coil 71 in a relatively friction-free manner. Therefore, the filament assembly 30 axially vibrates in the direction of arrows 47 and in response to alternating magnetic field 48. FIGS. 4, 6 and 7 also show a filament handle 46 which is employed for the manipulation of the filament assembly during its positional movement and placement onto the tympanic membrane.

FIG. 6 shows an alternate embodiment of the coil-based vibration force element 70 being cylindrically elongated and fully enclosing the magnetic vibratory element 45 within its core. The magnetic vibratory element 45 can be positioned within an operable range of several millimeters within or near the core of the coil while providing consistent and efficient dynamic coupling to the electromagnetic coil 71. As shown in FIGS. 4–7, the filament assembly 30, comprising the magnetic vibratory element 45, is readily removable from the vibration force element 70 simply by axially pulling apart the filament assembly from the core 74 of the vibration force element 70. FIG. 6 also shows a protective shield 73 for the vibration force element 70. The protective shield 73 may also incorporates material of proper characteristics for minimizing the affects of electromagnetic noise (electrical, magnetic, or both) present in the environment. FIG. 6 also shows an alternate configuration for the articulation between the filament shaft 40 and the tympanic coupling pad 60. In this case, the articulation is accomplished by providing a filament shaft with a magnetic tip 42 which is weakly attracted and articulated with a magnetic recess 64 within the coupling pad 60.

FIG. 7 shows an alternate embodiment of the vibration force element 70 comprising a disk-shaped coil 71. The magnetic vibratory element 45 is pin (rod) shaped and expands beyond the air core 74 area of the vibration force element as shown. Similarly, the dynamic coupling is consistent within an operable range spanning several millimeters to accommodate positioning the vibrational force element 70 within the individual ear canal and with respect to the individual tympanic membrane. FIG. 8 shows an alternate embodiment of a magnetic vibratory element 45 in the form of a tubular ring fitted over the filament shaft.

FIG. 7 also shows an alternate ball-joint articulation between the filament shaft 40 and tympanic coupling pad 60. In this particular embodiment, the ball socket 62 is formed by a race or a channel centrally positioned within coupling pad 60. The ball-joint system is self-lubricated or may comprise a ball-joint lubricant 63 (FIGS. 4 and 7) for facilitating the movement of the coupling pad with respect to the filament shaft 40. The coupling pad 60 may also be pre-coated by an interface contact agent 61 at its contact surface the tympanic membrane for enhancing the mechanical interface with tympanic membrane 20. The tympanic contact surface of coupling pad 60 or the contact agent 61 may be treated chemically, optically, or by the molding process to achieve various desired characteristics that include lubricity, wettability, antimicrobial, to conformity and adhesion. Contact agent 61, if used, is preferably a biocompatible gel, oil or like material, which provides weak adhesion forces between coupling pad 60 and tympanic membrane 20 for attachment of the filament assembly 30 to the tympanic membrane via the coupling pad 60 to allow for easy removal of the filament assembly. The desired contact characteristics of coupling pad 60 may also be achieved by appropriate selection of the pad material, without any contact agent 61, or by special surface treatment. For example, the pad material may be made of low durometer medical grade silicone or silicone gel which is soft and tacky.

Although the positional movement of the filament assembly 30 is shown as being primarily in the axial direction (one-degree of motion freedom), other degrees of motion freedom are also possible. For example, by expanding the air-core (FIG. 9) volume 74 between vibratory element 45 and vibration force element 70, a tilting positional motion is possible as indicated by arrow 49 and the tilted position of element 45 as shown in dashed lines. This degree of motion freedom is in addition to the axial positional motion freedom indicated by double-headed arrow 47.

The filament assembly is designed to impart audible vibrations on the tympanic membrane while fully absorbing any static and transient forces caused by positional changes of the hearing device or the tympanic membrane. Positional changes of the hearing device occur, for example, during device placement, removal or during epithelial migration of the skin within the ear canal. Positional changes of the tympanic membrane occur, for example, during sneezing or when atmospheric pressure rapidly changes (i.e., during an airplane ride).

In the preferred embodiment, the coupling to the tympanic membrane is achieved via a weak adhesion force between the filament assembly and the umbo area of the tympanic membrane. However, in alternative embodiments, riding adhesion methods (not shown) including glue and surgical attachment to the tympanic membrane or the malleus, are possible with techniques well known in the field of surgery, particularly related to the ear (see U.S. Pat. No. 5,015,224 to Maniglia; and Bojrab, D., "Semi-Implantable Hearing Device," Meeting of Triologic Society, Ann Arbor, Mich., Jan 24, 1988, pp. 11–12).

The filament assembly 30 of the present invention is designed to exert only vibrational (dynamic) pressures on the tympanic membrane. Dynamic coupling eliminates static forces which are potentially damaging to the tympanic membrane and the delicate structures associated with it. Static forces include push, pull and forces along the plane of the tympanic membrane. Static forces also cause distortion of perceived sound because of the directional bias associated with static pressure. Transient forces can also occur during ear canal movements caused by jaw motions as described above. Dynamic coupling between the filament assembly and the vibration force element virtually eliminate both static and transient pressures on the tympanic membrane. Furthermore, the removable dynamic coupling of the filament assembly offers safety during accidental or unintended motion of the hearing device or any part thereof. Since the filament assembly 30, or any part thereof, is likely to deteriorate with time due to its vibratory motion or the chemical environment in the ear, the detachability aspect of the filament assembly is ideal in disposable applications involving periodic replacement of the filament assembly.

Oxygen access to the covered part of tympanic membrane 18 can be enhanced by fabricating a tympanic coupling pad 60 from a material which is oxygen permeable. These materials are well known in the art of biomaterials (see, e.g., U.S. Pat. No. 4,540,761 to Kazunori et al). An oxygen permeable coupling pad may be particularly suitable for extended wear applications.

The articulation joint between the filament shaft 40 and coupling pad 60 may be permanently joined (FIG. 4 for example) or readily removable (FIG. 6 for example). A removable attachment approach, at either or both ends of the filament shaft, has the advantage of allowing individual parts of the hearing device to be easily attached and removed for installation, inspection, and replacement purposes.

Figure 10:
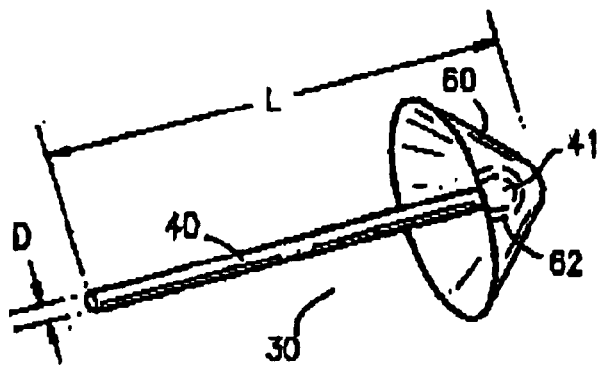
FIG. 10 is a perspective view of the vibrational filament assembly showing an umbrella-like tympanic coupling element articulating with the filament shaft via a ball joint system.
Figure 11:
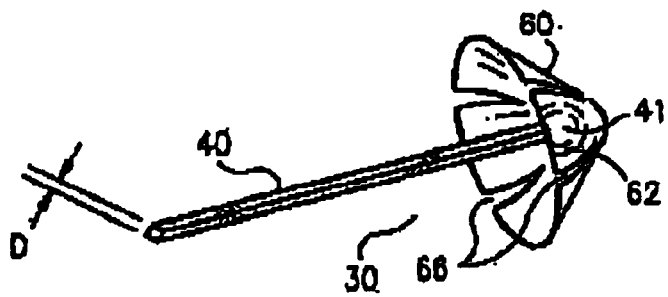
FIG. 11 is a perspective view of an alternate embodiment of the tympanic coupling element including slotted segments for improved conformity and contact within individual umbo areas.
Figure 12:
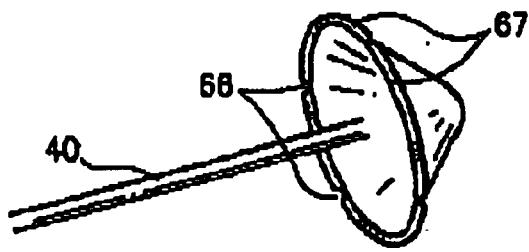
FIG. 12 is a perspective view of an alternate embodiment of the tympanic coupling element including slotted flaps at the rim for improving contact and sealing to minimize drying of contact agents and peeling effects at the contact surface.
Figure 13:
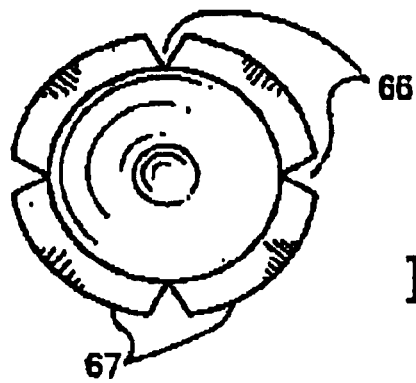
FIG. 13 is an end view of the embodiment shown in FIG. 12.
Figure 14A:
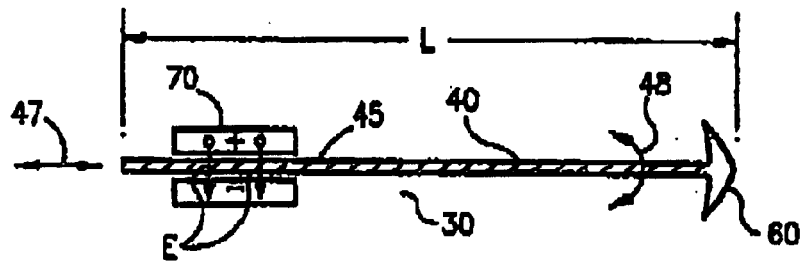
FIG. 14A is a sectional side view of a vibrational filament assembly, in the form of a thin strip, subjected to radial dynamic forces exerted by dynamic electrical field resulting in radial (rocking) vibrational motion, in which the filament assembly remains free to move axially for absorbing static and transient positional motion.
Figure 14B:
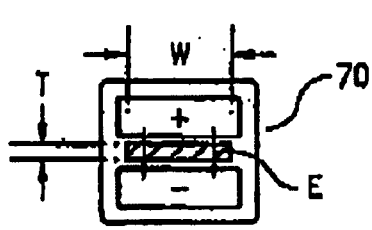
FIG. 14B is a cross sectional view of the embodiment of FIG. 14A showing the thickness (T) and width (W) of the thin strip filament placed within stationary plates producing electrical field (E) representative of audio signals.

The filament shaft 40 or the vibratory element 45 connected thereto, may be rod shaped having small diameter (D) preferably less than 0.4 mm., with a cross section that may be round or rectangular as shown in FIGS. 10 and 11, respectively. The filament shaft 40 or the vibratory element 45 may also be in the form of a thin strip as shown in FIGS. 14A and B and 15A and B, with a thickness (T) less than 0.4 mm. The length (L) of the filament assembly 30 (e.g., FIG. 14A) is preferably at least 6 mm. The ratio of length versus diameter (L/D), or length versus thickness (L/T) for a strip filament, is preferably greater than 25, thus substantially elongated in shape.

The filament assembly is preferably fabricated of light-weight material or of metals having very small dimensions, thus minimizing the weight while appropriately conducting vibrations to the tympanic membrane. The weight is preferably less than 20 mg. The material choice of the filament assembly, or any part thereof, ranges from plastics, ceramics, nylon, glass, titanium, steel, gold to metal alloys.

Although the filament assembly 30 is partially supported by the tympanic membrane 18, the apparent weight or inertial loading on the tympanic membrane is less than the actual weight. This is because the filament assembly is also rested on or supported partially by the vibration force element 70 which is stationary and has much greater weight than the filament assembly. Since the vibratory transduction occurs away from the tympanic membrane with minimal mass loading thereto, the energy efficiency of the vibratory transduction is significantly improved as compared with the above mentioned prior art, involving transducers directly positioned on the tympanic membrane.

The contact area of the coupling to the tympanic membrane is preferably at the umbo area 20, to provide optimal energy transfer by the lever action of the malleus. The shape of the coupling pad is preferably conical to match the natural shape of the umbo area, as shown in FIGS. 4, 6–7. Preferably, the coupling pad and the filament are shaped and designed to allow self-centering within the conic shape of the umbo area. The tympanic coupling pad 60 is therefore preferably mushroom or umbrella-shaped as shown in FIGS. 10 and 11. The coupling pad may also be slotted with radial cuts 66 (FIG. 11) for improving conformity and fit within the conic shape of the umbo area 20 of the tympanic membrane 18. The coupling pad may also be partially slotted as shown at 66 in FIGS. 12 and 13, with flexible flaps 67. These circumferential flaps enhance the contact fit and sealing of the coupling pad, thus minimizing evaporation and loss of the fluid contact agent 61 (e.g., FIG. 4) present on the surface of the tympanic membrane.

Other possible designs of the filament assembly include composite material and configurations (not shown). By combining two or more materials or segments of different physical properties, the overall characteristics may be optimized. For example, by combining strands each having optimal vibrational conduction in a particular different frequency range, the combined frequency response may be made greater than the individual response.

The vibrational forces of the filament shaft 30 are primarily axial (push/pull) as shown by arrows 47 in FIG. 4. However, other modes of vibration—for example, a rocking motion as shown by arrows 48 in FIGS. 14A and 15A—may be advantageous for human perception in certain frequency ranges or for individuals with certain anatomic orientation of the tympanic membrane.

Figure 15B:
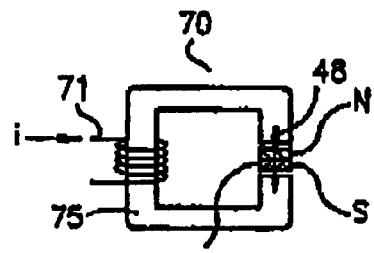
FIG. 15B is a cross sectional view of the embodiment of FIG. 15A showing the radial vibrational forces of the electromagnet on the vibrational filament assembly.
Figure 15A:
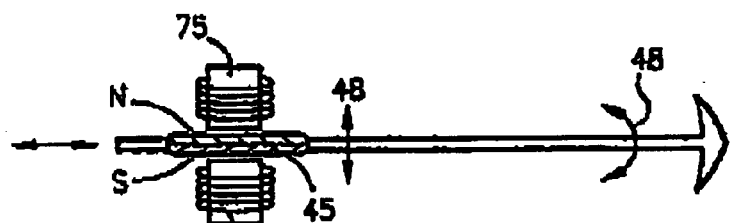
FIG. 15A is a side view of an alternate electromagnetic transducer embodiment having radial (rocking) magnetic forces by an electromagnet coil for exerting radial dynamic forces on the filament assembly, in which the filament assembly remains free to move axially for absorbing static and transient positional motion.

The vibratory conduction of the filament of the present invention is considerably more efficient than air-conduction or radiant electromagnetic conduction of the prior art. This is because the energy output of the vibratory transduction is more directly coupled to the tympanic membrane compared to the prior art. The vibration force element 70 used in the present invention can be of any suitable form for imparting mechanical vibrations to the floating filament assembly. In the preferred embodiments shown in FIGS. 4–9, the vibration force element comprises an axially oriented electromagnet coil. Other vibration force embodiments and configurations are possible as shown in FIGS. 14A–B, 15A–B and 16A–B. In FIGS. 14A and B, the vibration force element 70 produces an alternating electric field (E) which causes the vibratory element 45 of the filament assembly 30 to vibrate. The vibratory element 45 in this embodiment comprises a piezoelectric film element known to vibrate in response to an alternating electrical field. FIGS. 15A and B are side section and end views of an alternate electromagnetic coil embodiment with coil 71 would around a high permeability core 75 (i.e., soft iron). The resultant magnetic field (not shown) is radially oriented thus causing rocking vibrations in the direction of arrows 48. The magnet vibratory element 45, having north (N) and south (S) poles as shown, vibrates in response to an alternating magnetic field produced by alternating current (i) delivered through coil 71 originating from processing amplifier 92 (FIG. 3) of a hearing device 90 within the ear canal 10.

Figures 16A, 16B:
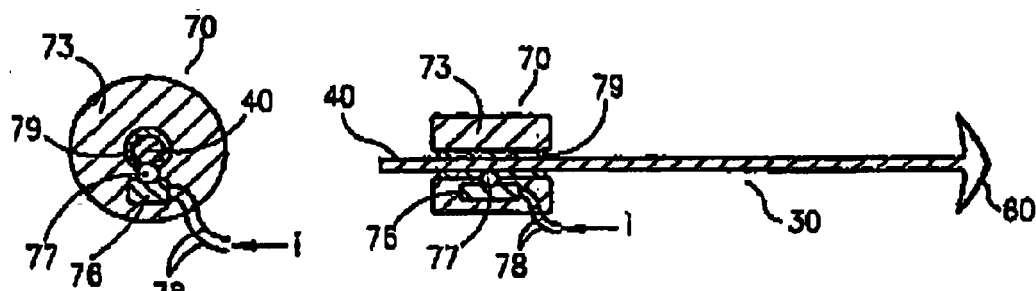
FIG. 16A is a sectional side view of an alternate embodiment of the vibration force element comprising a vibrational transducer with vibrating head.
FIG. 16B is a cross sectional view of the embodiment of FIG. 16A showing the contact relationship between the vibrating tip and vibratory element of the filament assembly.

In the embodiment shown in FIGS. 16A and B, the vibration force element 70 comprises a vibratory transducer 76 having a vibrational or vibrating element 77 (vibrational head, moving armature, etc.) which contacts the filament shaft 40 and transfers vibrations thereto. The vibrating element 77 may be in the form of a tip or a moving armature, as well known in the field of vibrational transducers. Similar to other embodiments, the filament shaft 40 is freely movable with respect to the vibratory transducer 76 to adjust the filament assembly 30 for proper contact with the tympanic membrane via the tympanic coupling pad 60. The vibratory transducer 76 produces vibration at its vibrating element 77 in response to alternating current (i) introduced into electrical wires 78 of the vibratory transducer 76. The vibratory transducer 76 is encapsulated by protective housing 73.

The interface between the vibratory element 45 of the filament assembly 30 and the vibration force element 70 may be formed by a gap (air-core) 74 as shown in FIGS. 6–7. The interface preferably comprises a lubricant 79 or a lubricated surface as shown in FIGS. 4, 16A and B. The lubricant is preferably of low-viscosity material to minimize friction between the floating filament assembly 30 and the stationary vibration force element 70.

The vibration force elements of FIGS. 4–16 are merely exemplary of possible force elements that may be used for imparting vibrational energy to the filament assembly of the present invention. Other vibratory transducers, known in the field of acoustics and electrochemical design, may also be suitable for use with the present invention. This includes electrostatic, electret, magnetostrictive, piezoelectric, moving coils and other configurations employing one or more magnets or coils (not shown).

Figure 17:
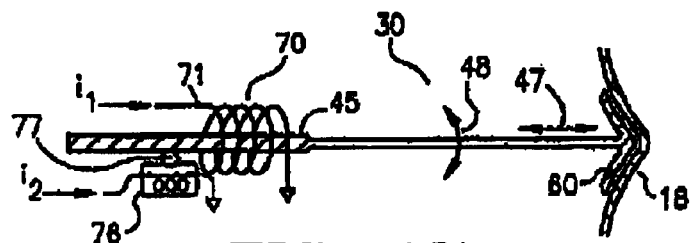
FIG. 17 is a sectional side view of an embodiment comprising dual vibration force elements combining electromagnet coil for producing axial vibrations and vibrational transducer for producing radial vibrations.
Figure 18:
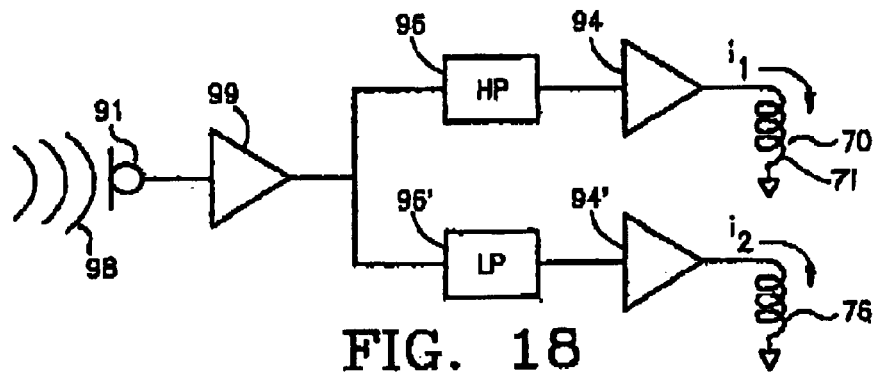
FIG. 18 is a simplified schematic diagram showing a two-band frequency splitter and two separate power outputs for stimulating two separate vibration force elements.

The present invention may comprise multiple vibration force elements to vibrate a filament assembly, and subsequently the tympanic membrane, in a variety of modes. For example, a combination of axial and radial vibrations may be produced to achieve a broader frequency response for an individual wearer. FIGS. 17 and 18 illustrate dual vibration force element system for achieving a combination of axial and radial vibration motions. A first vibration force element 70, comprising an electromagnetic coil 71, produces axial vibrations in the direction of arrows 47 when alternating current i is delivered through the coil. A second vibration force element 76, comprising a vibrating element 77, produces radial vibrations in the direction of arrows 48. The first and second vibration force elements, 70 and 76, may be electrically connected to separate output amplifiers 94 and 94', respectively, as shown in the exemplary circuitry of FIG. 18. The circuitry comprises a microphone 91 for receiving incoming acoustic signals 98, a preamplifier 99, a high-pass filter (HP) 96, a low-pass filter (LP) 96' and output amplifiers 94 and 94' connecting to first and second vibrational force elements 70 and 76, respectively.

Acoustic emissions are likely to develop within the ear canal due to the vibrations of the vibratory structures of the hearing device or the tympanic membrane. However, these acoustic emissions are far less than those emitted by conventional air-conduction hearing aids. Therefore, a hearing device of the present invention is relatively less prone to feedback than conventional hearing aids. Of course, feedback may occur for persons requiring a significant level of amplification. In these situations, feedback control measures must be provided as will be described below.

The present invention exploits its low power consumption and feedback reduction characteristics to create new device configurations not possible with conventional air-conduction or electromagnetic devices. This includes a total inconspicuous hearing device that is non-occlusive and suitable for extended wear within the ear canal.

Figure 19:
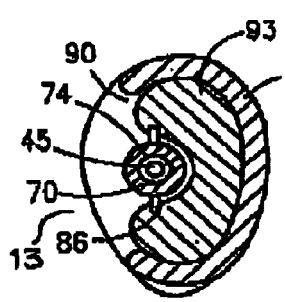
FIG. 19 is a cross sectional view of a hearing device embodiment showing the vibrational filament assembly within a pivoting vibration force element, and with C-shaped battery and device retainer wedged within the ear canal.

FIG. 3 shows a canal hearing device 90 of the present invention with the ear canal 10 non-occluded. This configuration alleviates many of problems found with occluding hearing devices of the prior art. Since there is no acoustic output by the canal hearing device, no sealing pressure is required to present feedback as is the case with conventional acoustic hearing devices. Therefore, the hearing device may be positioned in the ear canal with minimal skin contact and pressure. FIG. 19 shows a cross sectional view of the hearing device 90 positioned in the bony region 13. A non-occlusive retainer 80 provides stability for the canal device 90. Retainer 80 is preferably made of soft biocompatible material such as medical grade silicone or polyurethane foam. Stability of the canal device may also be achieved by applying a soft biocompatible adhesive (e.g., hydrogel) between the canal device and the skin of the ear canal (not shown).

Figure 20:
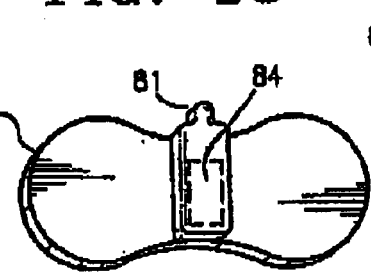
FIG. 20 is a perspective view of the retainer element having a single-wing arrangement and a peel-off tab for exposing its adhesive surface.
Figure 21:
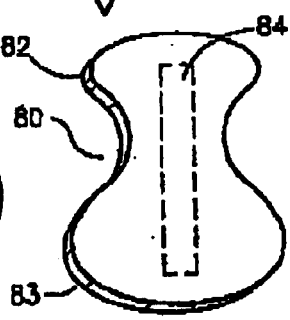
FIG. 21 is a perspective view of an alternate embodiment of the retainer element having a dual-wing arrangement.

The retainer 80 is preferably replaceable and disposable as shown in FIGS. 20 and 21. In the configuration of FIG. 20, the retainer is wing-shaped with a removable tab 81 for exposing an adhesive surface 84 for adhering the retainer 80 to the hearing device 90. In the dual-wing configuration of FIG. 21, the retainer 80 comprises a first wing 82, a second wing 83 and an adhesive surface 84 for adhering to the hearing device 90.

The non-occlusive retainer 80, shown in FIGS. 20 and 21 may be made in assorted sizes and shapes and is removably attachable to the hearing device. The retainer may be attached to hearing device 90 by conventional means such as pressure fit (not shown). The removable retainer is preferably disposable since it is likely to become soiled from debris present within the ear canal. Other retainer attachment methods (not shown) including clip and snap mechanisms, adhesion and magnetic attraction are possible as will be apparent to those skilled in the art. Similarly, the retainer may be made of oxygen permeable material for enhancing skin exposure to oxygen in the air.

By providing an assortment of retainers along with a universal device 90, the process of custom (individualized) fabrication as required in conventional hearing aids is eliminated. This leads to a mass producible device with benefits of lower production cost and improved product reliability.

For long term applications, the hearing device is preferably adapted to be positioned substantially in the bony portion of the ear canal to optimize its cosmetic aspects of inconspicuousness when worn, and to avoid interference with canal debris mostly present in the cartilaginous portion of the ear canal. Since the cartilaginous portion is mobile, placement of the hearing device in the immobile bony portion improves the stability of the device within the ear canal. The device or portions thereof may be treated with medication material to minimize possible contamination and infections within the ear canal. For example, the vibrational filament assembly or the associated hearing device may be composed of or treated by medication material such as anti-bacterial, anti-fungal, anti-microbial and like agents.

In deep canal applications, a person wearing the device has limited access for manual on/off control or adjustment of the device. However, various remote control methods are widely employed and known in the art of hearing aid and implant remote control and communications. A simple yet practical remote on/off control for the device of the present invention employs a latching reed switch (87 in FIG. 22) which responds to a magnetic field introduced into the vicinity of the canal hearing device. By providing the wearer with on/off magnetic device (not shown), the longevity of the battery can be further improved by turning off the power when the device is not needed (during sleep, for example).

Figure 28:
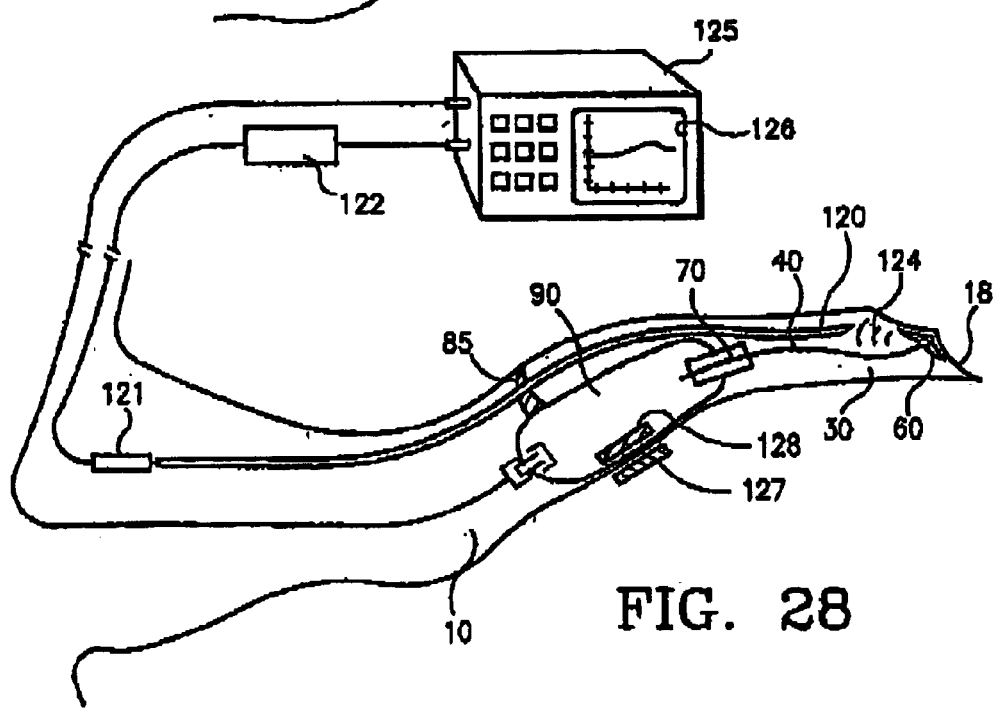
FIG. 28 is a view of a test setup employing probe tube acoustic measurement system for measuring the acoustic vibrations of a tympanic membrane in response to excitation by the vibrational filament assembly, and also illustrating a hearing aid fitting system.

As discussed above, in certain situations requiring high levels of amplification (i.e., severely impaired individuals), the acoustic emissions produced by the vibrated tympanic membrane may be enough to cause feedback. For these exceptional conditions, an acoustic screen 85 may be incorporated into the hearing device 90 as shown in FIG. 28. In this case, any occlusion effect attributable to the acoustic screen is not likely to be audibly perceived by persons with severe hearing impairment because of their elevated threshold of hearing. The acoustic screen may be functionally incorporated into the retainer if designed to be occlusive (not shown).

Figure 23:
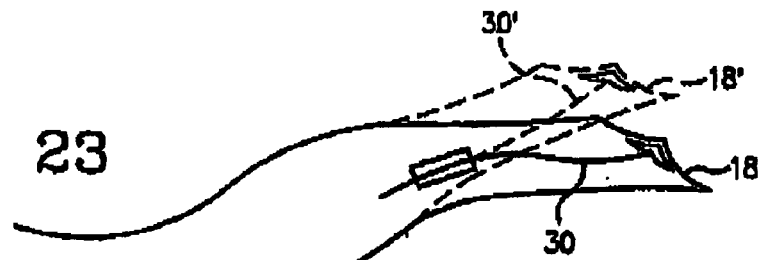
FIG. 23 is a sectional side view of the ear canal showing a relatively flexible filament shaft and the articulation of tympanic coupling element with two different shapes of the medical end of the ear canal.

FIG. 23 shows a flexible filament shaft of filament assembly 30, which may assume an alternate position (30') in order to fit optimally on the tympanic membrane 18 or 18', depending on the individual shape of the ear canal and the tympanic membrane.

Figure 24:
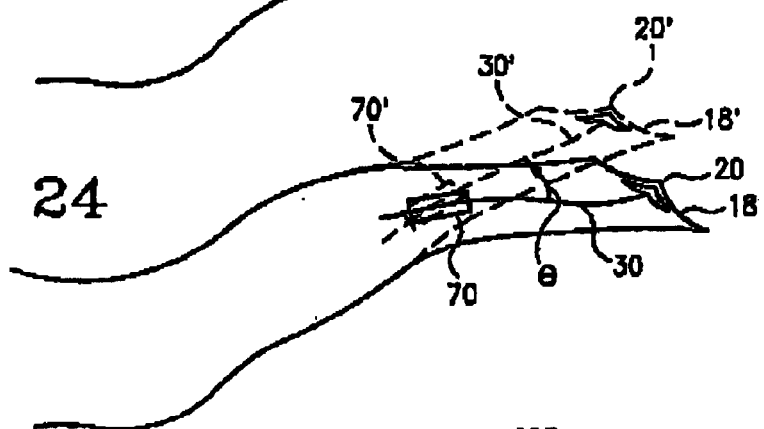
FIG. 24 is a sectional side view of the ear canal showing a pivoting vibration force element having adjustable projection angle to deal with individual variability in the orientation of the tympanic membrane with respect the ear canal.

In a preferred embodiment of the invention shown in FIG. 24, the vibration force element 70 preferably comprises an adjustable projection angle in order to project the filament assembly 30 placed therein directly onto the umbo area 20 of the tympanic membrane 18. In an alternate shape of the ear canal and the tympanic membrane, shown in dashed lines, the vibration force element 70' and the filament assembly 30' are positioned in a different projection angle in order improve the fit within umbo area 20' of the alternate tympanic membrane 18' in the alternate position. The adjustable projection angle may be achieved by incorporating a pivot joint 86 (i.e., pins) as shown in FIGS. 19 and 22 which project into a C-shaped battery assembly 93, partially surrounding the pivoting vibration force element 70.

Figure 22:
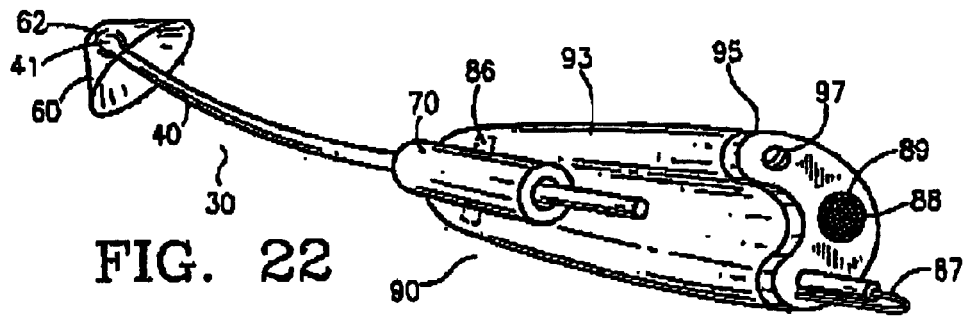
FIG. 22 is a perspective view of a hearing device embodiment of FIG. 19 showing the battery assembly, pivoting vibration force element and vibrational filament assembly.

FIG. 22 also shows lateral module 95 connected to battery assembly 93. The lateral module comprises latching reed switch assembly 87, microphone sound port 88, acoustically transparent microphone guard 89 for protecting the microphone from debris or moisture, volume control potentiometer 97, and other components typical of hearing aids (not shown). The battery assembly 93 is preferably removable and disposable but may also be rechargeable.

Periodic replacement of the battery assembly 93 and other disposable elements of the hearing device of the invention is not likely to be necessary before several months of use have elapsed, owing to its highly energy efficient design. The removable and disposable elements within the device include, for example, filament assembly 30 or portion thereof, battery assembly 93, device retainer 80, acoustic screen 85 and microphone guard 89.

Figure 25:
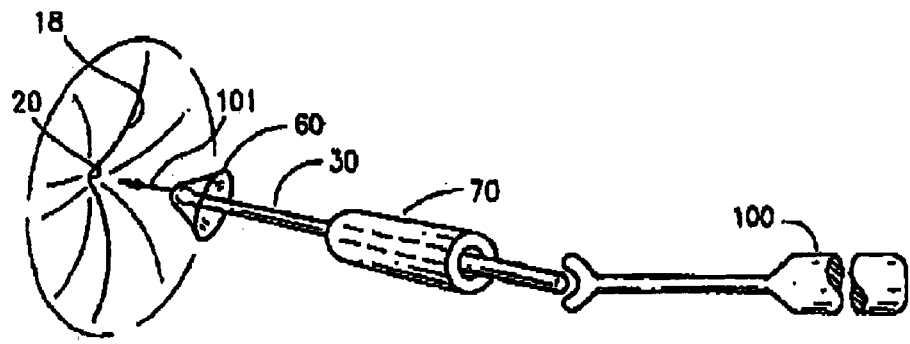
FIG. 25 is a perspective view illustrating the technique of manual manipulation of the filament assembly via its lateral handle by an elongated tool for placement into the umbo area.
Figure 26:
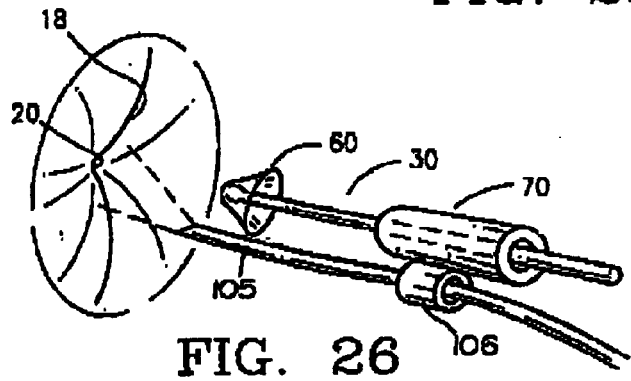
FIG. 26 is a perspective view illustrating the technique of suing a fiber optical probe held in a guide ring holder of a hearing device for viewing the tympanic membrane, for facilitating proper positioning of the vibrational filament assembly by viewing the tympanic membrane during the placement of the tympanic coupling element on the umbo area.

The manipulation of the filament assembly 30, for placement and removal onto and from the tympanic membrane 18, may be performed by a physician or an ear specialist (i.e. otolaryngologist, otologist, etc.) via a manipulation tool 100 as shown in FIG. 25 (hearing device not shown for the sake of clarity). The manipulation tool 100 can be used for pushing the filament assembly 30 and positioning the tympanic contact pad 60 in the direction of arrow 101 onto the umbo area 20 of the tympanic membrane 18. The manipulation tool 100 may consist of a curette, forceps, an ear loop, an ear hook or any other suitable tool generally available in otolaryngology offices. A pre-application of liquid contact agent 61 (i.e., mineral oil) on the tympanic membrane may be desirable for adhering the filament assembly to the tympanic membrane during the placement process.

In addition to direct visualization of the tympanic membrane using conventional lighting, an optical fiber 105 (FIG. 26) may be used to assist in the lighting and/or viewing of the tympanic membrane 18 while the filament assembly is being positioned on it. A guide 106 (shown as a ring holder in FIG. 26) is preferably employed for holding and guiding the optical fiber 105 within during the manipulation of the filament assembly in the ear canal.

Figure 27:
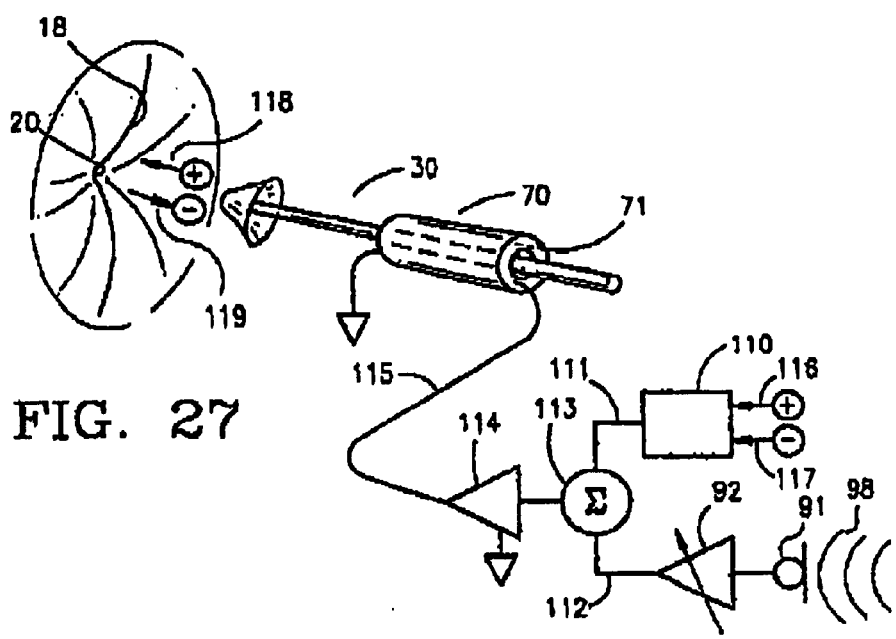
FIG. 27 is a partially perspective view and partially schematic representation showing advancement and retraction motion of the filament assembly by positional control circuitry in conjunction with vibrational motion for audibility by audio amplifier circuitry.

The manipulation of the filament assembly 30 may also be achieved by applying momentarily static forces via the vibration force assembly 70 which normally applies dynamic forces representative of acoustic signals. FIG. 27 demonstrates the combination of position control signals 111 from position control circuit 110 and audio signals 112 from signal processing amplifier 92. Incoming acoustic signals 98 are received by microphone 91 and amplified by signal processing amplifier 92. Signal processing amplifier 92 is shown separate but may be incorporated within microphone 91, as known in the art of hearing aid design. Position control signals 111 are combined with audio signals 112 at the summing circuit 113 for power amplification by power amplifier 114. The summed output 115 from power amplifier 114 is then delivered to the electromagnet coil 71 of the vibration force element 70. Upon triggering either a positive (+) control signal (arrow 116) or negative (−) control signal (arrow 117) at the input of the position control circuit 110, the filament assembly 30 will either move medially 118 or laterally 119, depending on the polarity of the control signal. Once the filament assembly is properly attached to the tympanic membrane 18, position control signals 111 are turned off while audio signals 112 are invoked to dynamically vibrate the filament assembly for audible perception by the tympanic membrane.

In order to verify the proper attachment of the filament assembly 30 to the tympanic membrane 18, the acoustic response resulting from tympanic vibrations can be measured. FIG. 28 shows an acoustic measuring system comprising test probe tube 120, probe tube microphone 121, microphone amplifier 122 and signal measuring device 125. The signal measuring device 125 also produces test signals, either electrical (as shown) or acoustic (via a speaker, not shown), for amplification by the in-situ hearing device. Once the filament assembly 30 of the hearing device 90 is properly connected to the tympanic membrane, the vibrations of the tympanic membrane produce an acoustic response 124 which is measured by the measuring instrument 125 and displayed on its display monitor 126. FIG. 28 is also representative of an external fitting system used for programming, diagnostics (including audiometric testing) and fitting of the in-situ hearing device connected to the measuring instrument 125.

FIG. 28 also shows an alternate retainer method for the hearing device 90 by employing an implant magnet 127 surgically positioned underneath the skin of the ear canal. The implant magnet 127 attracts a device magnet 128 (or a magnetic material—e.g. steel, battery case, etc.) contained within the hearing device 90.

The filament assembly of the present invention is not limited to hearing aid applications. Other applications include inconspicuous wireless communication systems. For example, an external audio device may be equipped with antenna for transmitting wirelessly a radio frequency (RF) signal to a receiver element within a canal hearing device (not shown). Other radiant wireless transmission types and configurations (not shown) are well known in the art of wireless communications and include, for example, ultrasonic, optical, infrared and microwave signals. The canal hearing device may be part of any communication system for inconspicuously imparting audio information to an individual wearing the vibratory filament assembly of the present invention. This includes telephone, "walkie-talkie", and other communication devices that should become apparent to anyone skilled in the art of communications once the principles of the disclosed invention are understood.

A significant advantage of the non-occlusive design of the present invention, whether for hearing aid or audio communication applications, is its ability to provide simultaneous dual sound perception. The first sound is conducted from the vibratory filament assembly as described above. The second sound is conducted to the tympanic membrane from outside the ear canal directly via air conduction in the non-occluded ear canal. This duality of sound perception has useful applications generally not possible with conventional hearing devices. In one example, a person with primarily high frequency loss may be provided with a hearing aid incorporating the filament assembly of the present invention for producing only high frequency vibrations, while relying on natural air-conduction for perceiving the low frequency sounds. In another example for communication applications, natural sounds from outside the ear canal are perceived simultaneously with privately perceived sounds via the communication device of the present invention.

Applications of the vibratory filament assembly for providing audible vibrations to the tympanic membrane are not limited to the above examples and should become obvious to those skilled in the art.

Although a presently contemplated best mode of practicing the invention has been disclosed herein by reference to certain preferred embodiments and methods, it will be apparent to those skilled in the art that variations and modifications of the disclosed embodiments and methods may be implemented without departing from the spirit and scope of the invention. It is therefore intended that the invention shall be limited only to the extent required by the appended claims and the rules and principles of the applicable law.

What is claimed is:

1. A filament assembly constructed and adapted to fit within the ear canal of an individual for contacting the tympanic membrane directly and imparting audible vibrations thereto, said filament assembly being operational relative to a stationary vibration force element positioned in the ear canal at a distance from the tympanic membrane, said filament assembly comprising:
   (a) a vibratory element adapted to be laterally positioned when said filament assembly is fitted within the ear canal, and arranged to respond to dynamic forces imparted by said vibrational force element, and
   (b) a vibrational shaft element extending medially for transferring audible vibrations from said vibratory element to the tympanic membrane when said filament assembly is fitted within the ear canal,
   said filament assembly being dynamically coupled to said stationary vibration force element so as to be statically floating and freely movable within an operable range with respect to said vibration force element, thereby allowing individual adjustment and positioning of said filament assembly for contacting the tympanic membrane and imparting audible vibrations without exerting static forces thereto.

2. The filament assembly of claim 1, wherein said vibrational shaft element is sufficiently axially rigid to efficiently conduct vibrational energy at audible frequencies to the tympanic membrane.

3. The filament assembly of claim 1, wherein said vibrational shaft element is radially flexible.

4. The filament assembly of claim 1, wherein the length of said filament assembly is at least 6 mm.

5. The filament assembly of claim 1, wherein the diameter (D) or thickness (T) of said vibrational shaft element and said vibratory element is less than 0.4 mm.

6. The filament assembly of claim 1, wherein the radio of length (L) of said filament assembly to diameter (D) or thickness (T) of said vibrational shaft element is greater than 25.

7. The filament assembly of claim 1, wherein said filament assembly is separable from said vibration force element for placement and replacement of the filament assembly onto and from the vibration force element.

8. The filament assembly of claim 1, wherein said filament assembly weights less than 20 mg.

9. The filament assembly of claim 1, wherein said vibratory element comprises a magnetic material which vibrates in response to a magnetic field produced from said vibration force element.

10. The filament assembly of claim 9, wherein said magnetic material of said vibratory element comprises a permanent magnet.

11. The filament assembly of claim 10, wherein said permanent magnet is rod shaped.

12. The filament assembly of claim 10, wherein said permanent magnet is cylindrically hollow.

13. The filament assembly of claim 1, further comprising a tympanic coupling element adapted to contact said tympanic membrane for transferring said audible vibrations thereto.

14. The filament assembly of claim 13, wherein said tympanic coupling element is articulated with respect to said vibrational shaft element via an articulation joint.

15. The filament assembly of claim 14, wherein said articulation joint comprises a ball and a socket system.

16. The filament assembly of claim 14, wherein said articulation joint comprises a rounded edge and a recess with magnetic attraction therebetween.

17. The filament assembly of claim 13, wherein said tympanic coupling elements is radially slotted.

18. The filament assembly of claim 13, wherein said tympanic coupling element comprises two or more circumferential flaps.

19. The filament assembly of claim 13, wherein said vibrational shaft element comprises a rigid material selected from a group comprising metal, glass, and plastics.

20. The filament assembly of claim 13, wherein said tympanic coupling element is removably attachable to the tympanic membrane by means providing a relatively weak adhesion force.

21. The filament assembly of claim 20, wherein said relatively weak adhesion force means includes a layer of biocompatible agent between said tympanic coupling element and the tympanic membrane for providing adhesion therebetween.

22. The filament assembly of claim 21, wherein said biocompatible agent is selected from a group comprising gel and oil.

23. The filament assembly of claim 21, wherein said biocompatible agent is non-drying for providing long term adhesion between said tympanic coupling element and the tympanic membrane.

24. The filament assembly of claim 13, wherein said tympanic coupling element is self-centering with respect to the umbo area of the tympanic membrane during attachment thereto.

25. The filament assembly of claim 13, wherein said tympanic coupling element is arranged and adapted for surgical attachment to one of either the tympanic membrane or the associated malleus ossicle.

26. The filament assembly of claim 13, wherein said tympanic coupling element is umbrella shaped.

27. The filament assembly of claim 13, wherein said tympanic coupling element comprises a conic contact surface to fit within the external umbo area of the tympanic membrane.

28. The filament assembly of claim 13, wherein said tympanic coupling element comprises a conforming surface for enhancing the contact with the external surface of the tympanic membrane.

29. The filament assembly of claim 28, wherein said conforming surface is selected from a group comprising silicone, rubber, and gel.

30. The filament assembly of claim 13, wherein said tympanic coupling element is compared of oxygen permeable material.

31. The filament assembly of claim 1, wherein said vibration force element comprises adjustable projection means for adjusting the projection angle of said filament assembly when dynamically coupled to said vibration force element.

32. The filament assembly of claim 1, wherein said vibration force element comprises an electromagnet coil.

33. The filament assembly of claim 32, wherein said electromagnetic coil comprises an air-core for accepting said filament assembly partially therein.

34. The filament assembly of claim 1, wherein said vibration force element comprises a vibrating element for directly vibrating said vibratory element of said filament assembly.

35. The filament assembly of claim 1, wherein said filament assembly conducts audible vibrations at least partially by means of axial motion of the filament assembly.

36. The filament assembly of claim 1, wherein said filament assembly conducts audible vibrations at least partially by means of rocking motion of the filament assembly.

37. The filament assembly of claim 1, wherein said filament assembly comprises an elongated this strip selected from a group comprising piezoelectric, piezomagnetic or magnetostrictive elements.

38. The filament assembly of claim 1, further comprising a handle for manipulation of said filament assembly during placement in and removal from the ear canal in association with said vibrational force element.

39. The filament assembly of claim 1, further comprising lubricous means for minimizing contact friction of said filament assembly with said vibration force element.

40. The filament assembly of claim 1, further comprising medication material selected from a group including anti-bacterial, anti-fungal and anti-microbial agents.

41. A canal hearing device adapted for directly contacting the tympanic membrane and imparting audible vibrations thereto, comprising:
 (a) a floating vibrational filament assembly for contacting the tympanic membrane at its medial end,
 (b) a stationary vibration force element positioned in the ear canal at a distance from the tympanic membrane and operably associated with said vibrational filament assembly,
 said vibrational filament assembly dynamically coupled to said vibration force element so as to be statically floating relative thereto and responsive to dynamic forces imparted by said vibration force element on said filament assembly for movement freely within an operable range in at least one degree of freedom with respect to said vibration force element, thereby allowing individual adjustment and positioning of said vibrational filament assembly for contacting the tympanic membrane and imparting audible vibrations without exerting essentially any static forces thereto.

42. The canal hearing device of claim 41, wherein said vibrational filament assembly is at least 6 mm in length and shaft element of said vibrational filament assembly having a diameter of less than 0.4 mm.

43. The canal hearing device of claim 41, wherein said vibrational filament assembly is separable from said vibrational force element for placement and replacement therein.

44. The canal hearing device of claim 41, wherein said vibrational filament assembly further comprises a vibratory element coupled to said vibrational filament assembly and responsive to dynamic vibration forces imparted by said vibration force element.

45. The canal hearing device of claim 44, wherein said vibratory element is composed of magnetic material for responding to magnetic field produced from said vibration force element.

46. The canal hearing device of claim 44, wherein said vibratory element is responsive to a vibrating element incorporated within said vibration force element.

47. The canal hearing device of claim 41, wherein said vibrational filament assembly further comprising a tympanic coupling element adapted to contact the tympanic membrane for transferring said audible vibrations thereto.

48. The canal hearing device of claim 47, wherein said tympanic coupling element is articulated with respect to shaft element of said vibrational filament assembly via an articulation joint comprising a ball and a socket system.

49. The canal hearing device of claim 47, wherein said tympanic coupling element is adapted for removable attachment to the tympanic membrane by means providing a relatively weak adhesion force.

50. The canal hearing device of claim 49, wherein said relatively weak adhesion force means includes a layer of biocompatible agent between said tympanic coupling element and the tympanic membrane for providing adhesion therebetween.

51. The canal hearing device of claim 50, wherein said biocompatible agent is selected from a group comprising gel and oil.

52. The canal hearing device of claim 47, wherein said tympanic coupling element is self-centering with respect to the umbo area of the tympanic membrane during attachment thereto.

53. The canal hearing device of claim 47, wherein said tympanic coupling element is substantially umbrella-shaped.

54. The canal hearing device of claim 41, wherein said vibration force element comprises adjustable projection means for adjusting the projection angle of said vibrational filament assembly when dynamically coupled to said vibration force element.

55. The canal hearing device of claim 41, wherein said vibrational filament assembly is arranged and adapted to at least partially undergo axial motion to conduct audible vibrations to the tympanic membrane.

56. The canal hearing device of claim 41, wherein said vibrational filament assembly is arranged and adapted to at least partially undergo rocking motion to conduct audible vibrations to the tympanic membrane.

57. The canal hearing device of claim 41, further including retainer means for stabilizing and securing said canal hearing device within the ear canal of the wearer.

58. The canal hearing device of claim 57, wherein said retainer means comprises one or more pairs of foldable wings.

59. The canal hearing device of claim 57, wherein said retainer means comprises a biocompatible adhesive for adhering and securing said hearing device to the walls of the ear canal.

60. The canal hearing device of claim 41, comprising a hearing aid constructed and adapted to be worn completely within the ear canal of a hearing impaired individual.

61. The canal hearing device of claim 41, wherein said hearing device is constructed and adapted to be positioned substantially within the bony portion of the ear canal of the wearer.

62. The canal hearing device of claim 41, wherein said hearing device provides a highly energy efficient system, by virtue of directly vibrating the tympanic membrane, sufficient to enable said hearing device to be operational in the ear canal of the wearer for a period exceeding two months before dissipation of its battery to an extent requiring replacement of said hearing device or said battery.

63. The canal hearing device of claim 41, further including remote control means adapted to be positioned substantially external to the ear canal of the wearer of said hearing device for adjusting and controlling said hearing device worn in the ear canal of said wearer.

64. The canal hearing device of claim 63, further including a magnetically activated switch, and wherein said remote control means comprises an external magnetic device for operating said magnetically activated switch.

65. The canal hearing device of claim 41, further including an acoustically transparent debris guard for protecting a microphone of said canal hearing device against damage from moisture and debris present in the ear canal.

66. The canal hearing device of claim 41, comprising a plurality of removable disposable elements including said vibrational filament assembly, a battery, an acoustically transparent debris guard, an acoustic screen, and a device retainer.

67. The canal hearing device of claim 41, further including an external fitting system connectable to said canal hearing device for conducting audiometric evaluation, device programming and fitting prescription for a subject wearing said hearing device.

68. The canal hearing device of claim 41, comprising a wireless receiver for receiving wireless signals representative of audio signals from an external audio transmitter, said hearing device being responsive to received wireless signals for conversion thereof to audible vibrations representative of said audio signals.

69. The canal hearing device of claim 41, wherein said vibration force element comprises at least one electromagnetic coil.

70. The canal hearing device of claim 69, wherein said electromagnet coil comprises an air-core for accepting part of said vibrational filament assembly therein.

71. The canal hearing device of claim 41, wherein said vibration force element comprises at least one vibrational transducer having a vibrating element.

72. The canal hearing device of claim 41, wherein said vibration force element comprises a shield for minimizing at least one of electrical noise signals or magnetic noise signals present in the environment.

73. The canal hearing device of claim 41, comprising means for rendering said hearing device substantially non-occlusive within the car canal of the wearer to avoid occlusion effects.

74. The canal hearing device of claim 41, comprising means for rendering said hearing device substantially non-occlusive within the ear canal of the wearer to enable simultaneous perception of sound though vibratory conduction via said vibrational filament assembly, and through air-conduction via air the non-occluded ear canal.

75. The canal hearing device of claim 41, comprising means for manipulating said vibrational filament assembly for attachment to the tympanic membrane in cooperation with an external manual tool adapted for at least partial insertion into the ear canal.

76. The canal hearing device of claim 41, comprising means for manipulating said vibrational filament assembly for attachment to the tympanic membrane in cooperation with an optical fiber for enhancing viewing of said manipulation and attachment.

77. The canal hearing device of claim 41, comprising means for manipulating said vibrational filament assembly for attachment to the tympanic membrane in cooperation with a probe tube and corresponding probe tube acoustic measurements.

78. The canal hearing device of claim 41, comprising means for manipulating said vibrational filament assembly for attachment to the tympanic membrane in cooperation with momentary static forces generated by said vibration force element.

79. The canal hearing device of claim 41, further comprising lubricous means for minimizing contact friction between said vibrational filament assembly and said vibration force element.

80. The canal hearing device of claim 41, further comprising magnetic material for attraction to a magnetic implant surgically positioned in the ear canal underneath the skin, for securing said hearing device within said ear canal.

81. The canal hearing device of claim 41, further comprising medication material selected from a group including anti-bacterial, anti-fungal and antimicrobial agents.

82. A hearing device constructed and adapted to fit and be worn within the ear canal of a human subject for imparting audible vibrations to the tympanic membrane of the subject, comprising:
  a microphone for receiving the incoming signals representative of audio signals and converting them to electrical signals;
  an amplifier for processing and amplifying the electrical signal output of the microphone;
  a vibration force element responsive to said amplified signals for conversion thereof to dynamic forces representative of said incoming signals; and
  a vibrational filament assembly dynamically coupled to said vibration force element and responsive to said dynamic forces imparted by said vibration force element,
  said vibrational filament assembly being essentially free floating within an operable range in at least one degree of freedom with respect to said vibration force element, thereby allowing individual adjustment and positioning of said vibrational filament assembly for contacting the tympanic membrane and imparting audible vibrations without exerting essentially any static forces thereto.

83. The hearing device of claim 82, wherein said vibrational filament assembly further comprises:
  (a) an umbrella-shaped tympanic coupling element for contacting and adhering to said tympanic membrane and conducting vibrations thereto, and
  (b) a vibrationally conductive shaft articulated with said tympanic coupling element.

84. A method of imparting audible vibration on the tympanic membrane of an individual comprising the steps of:
  (a) attaching a vibratory filament assembly at its medial end to the tympanic membrane; and
  (b) dynamically coupling said vibratory filament assembly to a vibration force element so that said vibrational filament assembly is essentially free floating within an operable range, in at least one degree of motion freedom, with respect to said vibration force element to allow individual adjustment and positioning of said vibrational filament assembly for contacting the tympanic membrane; and (c) imparting mechanical vibrations representative of audio signals on the lateral end of said vibratory filament assembly by means of said vibration force element so as to impart audible vibrations to the tympanic membrane without exerting essentially any static forces thereon.

85. The method of claim 84, including employing a tympanic coupling element at said medial end of said vibratory filament assembly for contact with the tympanic membrane.

86. The method of claim 85, including providing weak adhesion forces between the surface of said tympanic coupling element and the tympanic membrane so that said tympanic contact element is removably attachable to the tympanic membrane, said weak adhesion forces being sufficiently strong to secure said tympanic coupling element to the tympanic membrane and conduct audible vibrations thereto.

87. The method of claim 86, including providing said weak adhesion forces as least partially by applying a thin layer of biocompatible liquid agent between the surface of said tympanic coupling element and the tympanic membrane.

88. The method of claim 85, including pre-coating the tympanic membrane with a liquid agent for adhering said tympanic coupling element to the tympanic membrane.

89. The method of claim 85, including joining said tympanic coupling element by articulation means to a shaft element of said vibratory filament assembly for articulating and adjusting said tympanic coupling element according to individual tympanic membranes.

90. The method of claim 89, including using a ball joint system as said articulation means.

91. The method of claim 85, including shaping said tympanic coupling element for fitting and securing thereof within the external umbo area of the tympanic membrane.

92. The method of claim 84, including manipulating and attaching said vibratory filament assembly to the tympanic membrane at least in part by any of direct visualization, optical fiber visualization, acoustic probe tube measurements and momentary static forces.

\* \* \* \* \*